(12) United States Patent
Henniges et al.

(10) Patent No.: US 8,905,413 B2
(45) Date of Patent: Dec. 9, 2014

(54) METHOD FOR COMPACTING SOLID MEDICAL WASTE

(71) Applicant: Stryker Corporation, Kalamazoo, MI (US)

(72) Inventors: Bruce Henniges, Galesburg, MI (US); Douglas L. Tyler, Paw Paw, MI (US); James G. Walen, Kalamazoo, MI (US); Chunwu Wu, Texas Township, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/955,538

(22) Filed: Jul. 31, 2013

(65) Prior Publication Data

US 2013/0333328 A1    Dec. 19, 2013

Related U.S. Application Data

(60) Division of application No. 12/761,928, filed on Apr. 16, 2010, now abandoned, which is a continuation of application No. PCT/US2008/080170, filed on Oct. 6, 2018.

(60) Provisional application No. 60/980,964, filed on Oct. 18, 2007.

(51) Int. Cl.
| | |
|---|---|
| *A61L 11/00* | (2006.01) |
| *B09B 3/00* | (2006.01) |
| *B65F 1/14* | (2006.01) |
| *B30B 9/30* | (2006.01) |

(52) U.S. Cl.
CPC ............ *A61L 11/00* (2013.01); *B09B 3/0075* (2013.01); *B65F 2210/188* (2013.01); *B65F 2210/167* (2013.01); *B65F 1/1415* (2013.01); *B65F 1/1468* (2013.01); *B30B 9/3007* (2013.01); *B65F 2210/1525* (2013.01)
USPC ........................................ 280/47.26; 383/100

(58) Field of Classification Search
USPC ........... 383/100, 103; 280/47.26, 47.35, 79.2; 53/434, 436
See application file for complete search history.

(56) References Cited

U.S. PATENT DOCUMENTS

| | | | |
|---|---|---|---|
| 4,448,434 A | | 5/1984 | Anderson |
| 4,670,227 A | * | 6/1987 | Smith ........................... 422/297 |

(Continued)

FOREIGN PATENT DOCUMENTS

| | | |
|---|---|---|
| KR | 20-0362209 Y1 | 9/2004 |
| KR | 20-0372667 Y1 | 1/2005 |

OTHER PUBLICATIONS

"KR Intel. Prop. Off. ISA Search Report and Written Opinion" for PCT/US2008/080170, Apr. 2009.

*Primary Examiner* — John Walters
*Assistant Examiner* — Brian Swenson

(57) ABSTRACT

A system for collecting and compressing waste collected in a medical or surgical procedure. The system includes a bag for collecting the waste that is seated on a mobile cart. Once the waste is collected the bag is closed and, while on the cart, transported to a compactor. While on the cart, the bag is compacted. Air in the bag is discharged through a one-way valve fitted to the bag. The one way valve may be attached to a cartridge that is inserted into the bag opening. The air discharged from the bag is filtered prior to discharge into the ambient environment. The filter may be built into the one-way valve.

24 Claims, 18 Drawing Sheets

(56) References Cited

U.S. PATENT DOCUMENTS

| | | |
|---|---|---|
| 4,809,915 A | 3/1989 | Koffsky et al. |
| 4,917,393 A | 4/1990 | Rogers |
| 5,001,425 A | 3/1991 | Beling et al. |
| 5,195,649 A | 3/1993 | Wolters |
| 5,228,271 A * | 7/1993 | Wallace ............... 53/434 |
| 5,339,959 A | 8/1994 | Cornwell |
| 5,389,346 A * | 2/1995 | Copeland, Jr. ............. 422/292 |
| 5,401,444 A * | 3/1995 | Spinello ............... 264/0.5 |
| 5,445,398 A | 8/1995 | Pierce |
| 5,659,247 A | 8/1997 | Clements |
| 6,045,264 A | 4/2000 | Miniea |
| 6,126,183 A | 10/2000 | Lensing |
| 6,222,450 B1 | 4/2001 | Clements |
| 6,352,225 B1 | 3/2002 | Dooley et al. |
| 6,375,131 B1 | 4/2002 | Youst |
| 6,651,942 B1 | 11/2003 | Yardley et al. |
| 6,833,789 B1 | 12/2004 | Carmen et al. |
| 7,114,629 B2 | 10/2006 | Panek |
| 7,484,275 B2 | 2/2009 | Carroll et al. |
| 2004/0000904 A1 | 1/2004 | Cotter |
| 2004/0222335 A1 | 11/2004 | Panek |
| 2009/0012485 A1 | 1/2009 | Michaels et al. |

\* cited by examiner

METHOD FOR COMPACTING SOLID MEDICAL WASTE

RELATIONSHIP TO EARLIER FILED APPLICATIONS

This application is a continuation of U.S. patent application Ser. No. 12/761,928 filed 16 Apr. 2010, now abandoned. U.S. patent application Ser. No. 12/761,928 is a continuation of PCT Pat. App. No. PCT/US2008/080170 filed 16 Oct. 2008. PCT Pat. App. No. PCT/US2008/080170 is a nonprovisional of U.S. Pat. App. No. 60/980,964 filed 18 Oct. 2007. The above-listed priority applications are incorporated herein by reference

FIELD OF THE INVENTION

This invention relates generally to a system for storing solid medical waste. More particularly, this invention is directed to a system and method for compacting solid medical waste so that it can be easily stored and handled.

BACKGROUND OF THE INVENTION

When a medical or surgical procedure is performed, more often than not, solid waste is generated. Generally, this type of waste falls into one of three categories. There is conventional trash. This type of waste consists of solid articles such as packaging material that is not contaminated with tissue or bodily fluids. A second type of waste is not truly "waste" but the linens used during the procedure. These linens, towels and sheets, are used for such purposes as stabilizing the patient or cleaning up liquids. Often these linens, even those covered in bodily fluids, can be sterilized, cleaned and reused. The third type of solid waste is the solid articles that, during the procedure become coated or exposed to bodily fluids. These articles include disposable wipes used at the surgical site and disposable medical instruments. Post use, these articles need to be disposed of in a manner that ensures the biological material they carry does not serve as a source of infection. Often, this material is called "red bag" waste.

During the course of a procedure these waste articles are, upon initial discarding, stored in portable carts in the operating room or other space in which they are generated. In some medical facilities, three carts are provided, one for storing each type of waste. The circulating nurse, or other individual that receives the waste from the person discarding it, is responsible for initially categorizing the waste and placing it in the appropriate cart.

When a bag containing either conventional waste or red bag waste is at or near capacity, it is sealed. At that time, the bag is transported to a loading dock for eventual transport to a waste processing facility.

The current waste handling systems do an adequate job of containing the waste articles prior to their eventual transport to a processing facility. Nevertheless, there are some disadvantages associated with the current systems. One problem is that during the placement of articles in one of the operating room carts, articles that are not waste are inadvertently placed in the cart. Typically, these articles are surgical instruments and articles that are not disposable. These articles are sterilizable and reusable. Another type of article that can sometimes end up in one of the waste carts is a specimen container that contains tissue harvested for a study. Both surgical instruments and specimen containers can inadvertently end up in waste cart because the person handling these articles is, at the same time, disposing an article that should go in the cart.

Another disadvantage of the present waste handling systems is due to the presence of the biological material that coats some of the waste. When this material is held in a bag for collection, it can start to generate odors that are highly offensive. These odors make it unpleasant for personnel to handle the bags in which this material is contained.

Further, it should be appreciated that the biological materials can include contaminates. Accordingly, the individuals handling bags containing these materials run the risk of inadvertent exposure to these contaminates. Also, an appreciable fraction of these biological materials are in the liquid state. These fluids have been known to leak out of a bag during handling. Also, when in the liquid state, these biological materials, with their contaminates, have been known to become aerosolized. When this happens more persons than those responsible for handling the bag run the risk of exposure.

Further, the bags in which the waste from plural procedures are stored can become rather heavy. As these are bags are simple plastic bags, the combination of weight and bulk can make them difficult handle.

DETAILED DESCRIPTION

Figure 1:
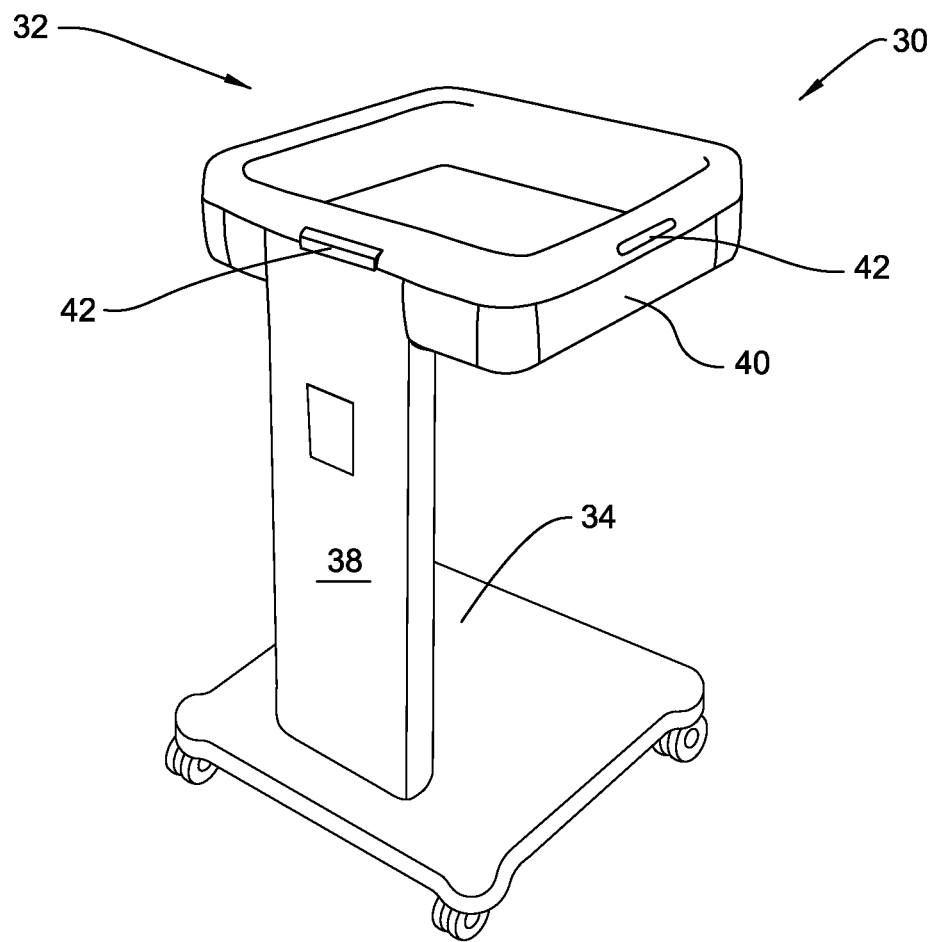
FIG. 1 is a perspective view of a cart of this invention, the view being of the back of the cart.
Figure 2:
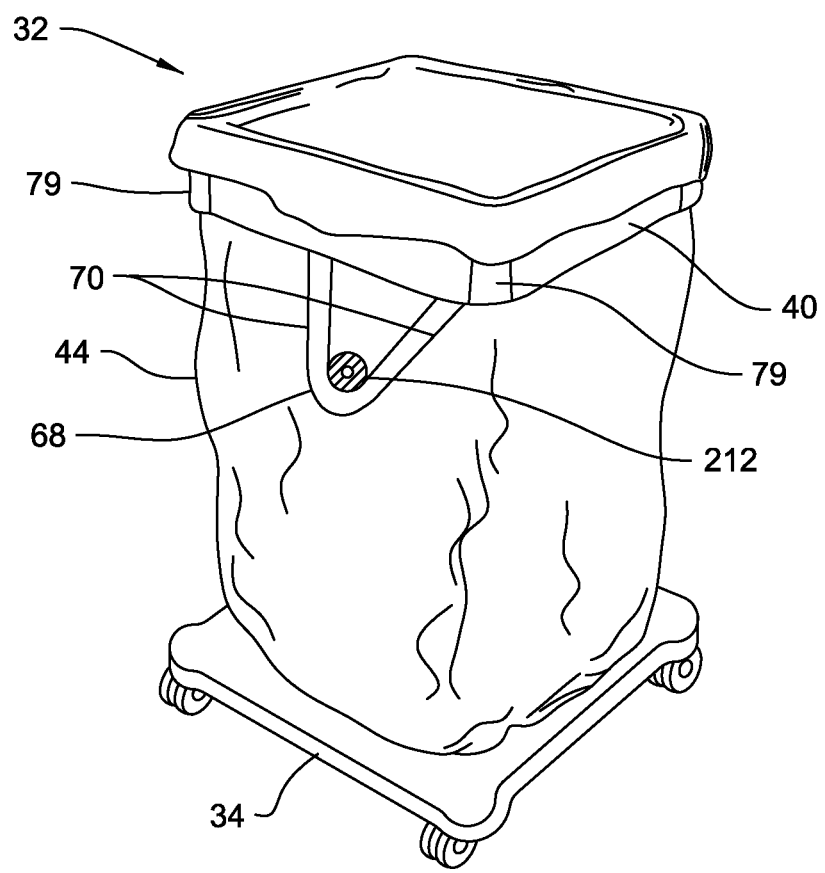
FIG. 2 is a perspective view of the front of the cart with a bag fitted to the cart, the flaps at the top of the bag being folded over the inner and top surfaces of the cart frame.
Figure 3:
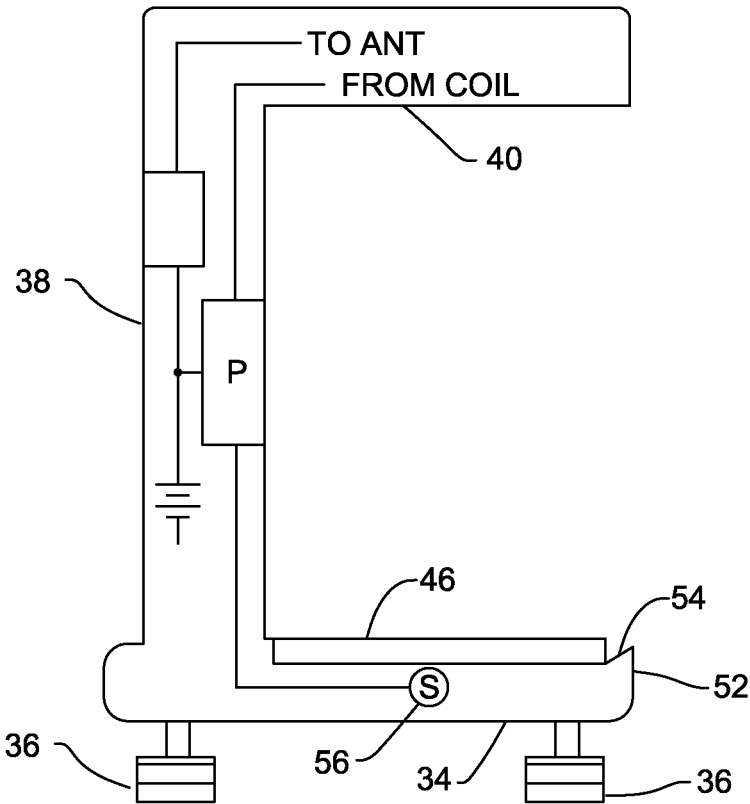
FIG. 3 is a diagrammatic view of the cart taken from the side of the cart.

One component of the solid waste management system 30 of this invention is a cart 32 seen in FIGS. 1-3. Cart 32 includes a planar base 34. Casters 36 mounted to the bottom of base 34 provide cart 32 with mobility. A rectangular leg 38 extends upwardly from one side of base 34. Leg 38 suspends an open rectangular frame 40 above the base 34. A number of tabs 42 project outwardly from the outer surfaces of frame 40. Tabs 42 are the structural members that hold the open the top of a bag 44 in the frame 40.

Figure 3A:
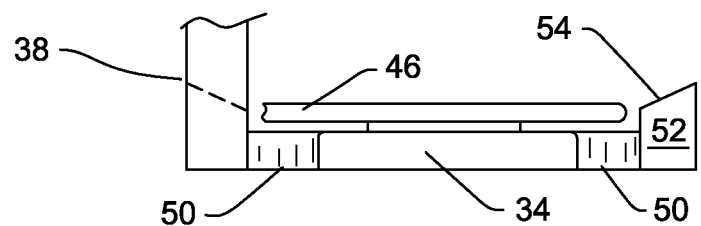
FIG. 3A is a side diagrammatic view of the lower portion of the cart, casters omitted, showing the base plate and overlying compression plate.
Figure 4:
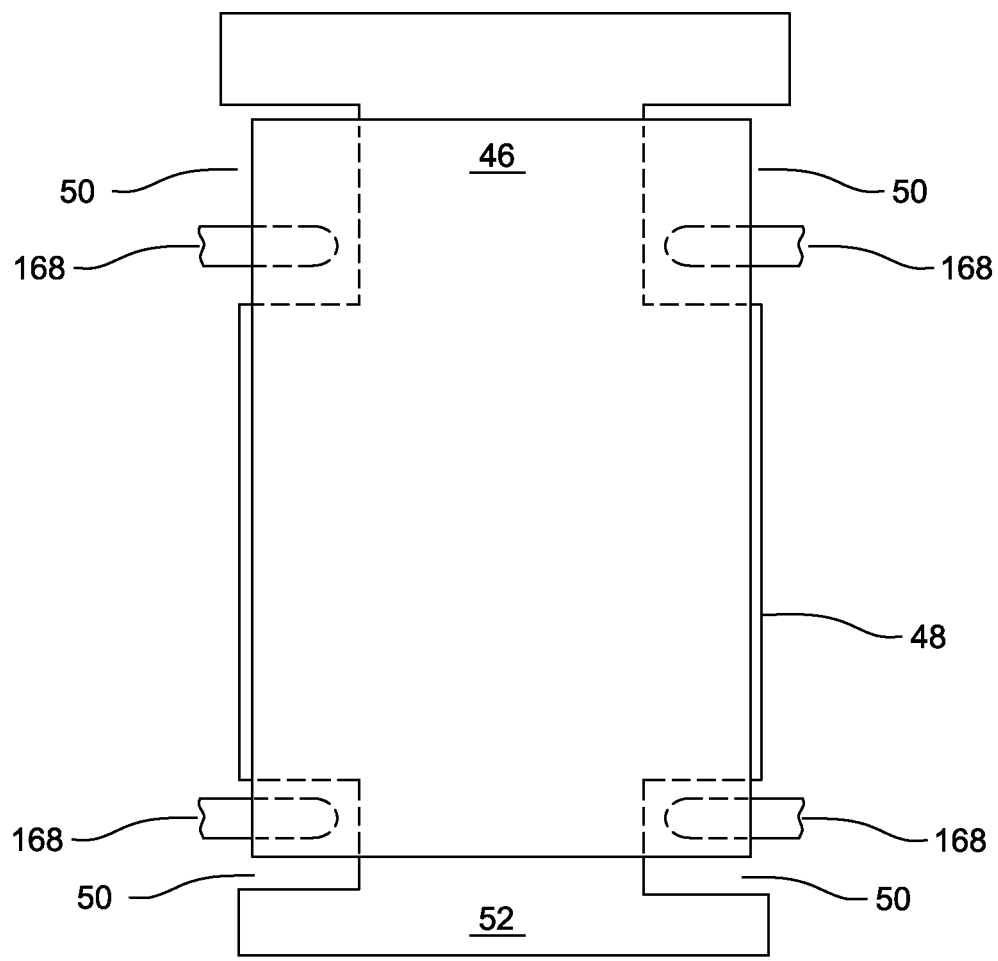
FIG. 4 is a plan view of how the compression plate seats over the base of the cart an fingers integral with the compactor lift frame move the compression plate up and down.

From FIGS. 3, 3A and 4, it can be seen that base 34 is not the primary component of the system 30 on which the bag is seated. Instead, base 34, supports a compression plate 46 that is moveably seated on the top of the base. More particularly, base 34 has a center panel 48. While the center panel 48 is planar and generally four-sided, geometrically, it is not exactly rectangular. Center panel 48 is further formed to define four notches 50. Each notch 50 is located where two of the perpendicular sides of the panel 48 would otherwise meet.

Base 34 is further formed so that at the front end, the end opposite the end from which leg 38 extends, there a beam 52 extends across the end of the base. Beam 52 thus defines the forward parameters of the two most forward notches 50. Generally beam 52 extends above the planar surface of panel 48. The beam 52 is formed to have a top surface 54 that is tapered such that extending front to rear along the surface the surface angles downwardly toward the adjacent surface of panel 48.

A pressure sensitive transducer 56 is disposed on the planar top surface of panel 48. Transducer 56 is the actual component of the base 34 on which compression plate 46 rests. The compression plate 46 itself is rectangular. Compression plate 46 is further dimensioned so that, when the plate rests over panel 48, the corners of the plate extend over notches 50.

Figure 5:
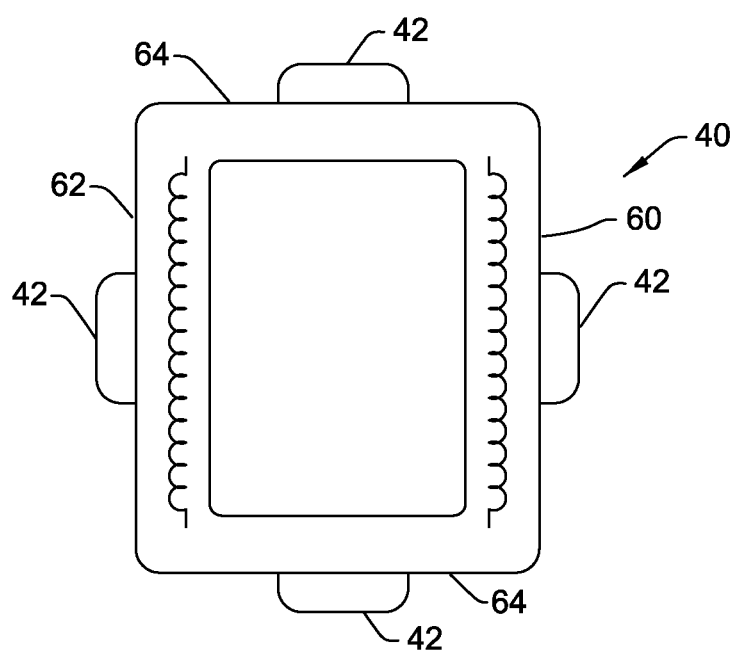
FIG. 5 is a plan view of the cart frame, the coils in the frame are depicted schematically.

Rectangular frame 40, seen in FIG. 5, is formed from plastic or other material that does not effect the transmission of electromagnetic waves. Frame 40 is rectangular in that front and rear webs 60 and 62, respectively, of the plate are longer than the associated front-to-rear extending lateral webs 64. A tab 42 protrudes outwardly from each web 60, 62 and 64.

Collectively webs 60, 62, 64 define an opening 58 in the frame 40. Each web 60, 62, 64 has an inner surface 57 that defines the outer perimeter of frame opening 58. A top surface 59 extends outwardly from each web inner surface 57. An outer surface 61, opposite the inner surface 57, extends downwardly from each top surface 59. Tabs 42 extend outwardly from the web outer surfaces 61.

First and second coils 65 and 66, respectively are disposed in, respectively the front web 60 and rear web 62. Each coil 65 and 66 is located between the inner and outer surfaces 57 and 61, respectively of the web 60 or 62 in which the coil is seated. Collectively, coils 65 and 66 function as a sensor assembly that detects when metal is placed into the bag 44.

Figure 6:
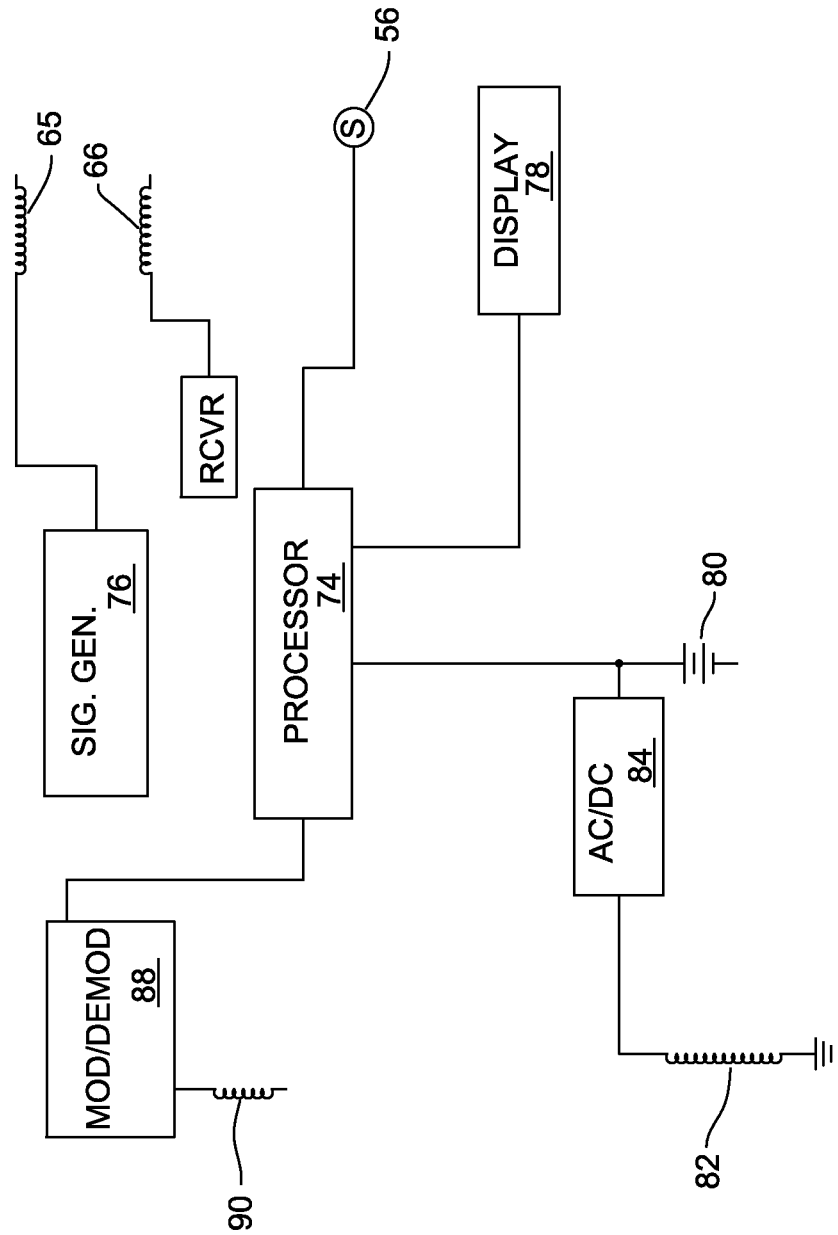
FIG. 6 is a block diagram of the electrical components integral with the cart.

Cart 32 is further formed to have a saddle 68 that is located below the front web 60. Saddle 68 is in the form of a U-shaped plate that may be made from metal or plastic. Two beams 70 that extend downwardly from the front web 60 suspend the saddle 68. In the illustrated version of the invention, each beam 70 extends diagonally both upwardly from the saddle 68 and away from the side of the side of the saddle to which the beam is attached FIG. 6 is a block diagram of the circuit components integral with cart 32. These components include a processor 74. A signal generator 76 generates the AC signal that is output by one of the coils, arbitrarily, first coil 65. Cart 32 also has a display 78. In some versions of the invention an enunciator, an audible alarm, is integral with the display 78. In some versions of the invention, one or more separately actuated lights 70 attached to the corners of the frame 40 are part of the display 78. A battery 80 powers the components internal to the cart 32. In most versions of the invention, the battery 80 comprises a set of rechargeable cells. Not illustrated is the voltage regulator(s) that output signals at the potentials required by the power consuming components integral with the cart 32. Also not illustrated are all the connections from the battery to which the power sourced by the battery is applied.

Also internal to the cart 32 is a receiver 82. Receiver 82 is connected to second coil 66 to covert the signals developed across the coil into a form in which they can be processed by processor 74. The signal produced by transducer 56 is also applied to processor 74 as in input signal. Not illustrated are any amplifiers needed to amplify the signal from the transducer 56 prior to application to the processor.

Two additional coils 82 and 90 are also part of the circuit internal to cart 32. Coil 82 is a coil configured to receive energy that is inductively transmitted to the cart 32. As described below, the cart is periodically placed in a compactor 140 (FIG. 8) that compresses the waste in the bag 44. When the cart 32 is so positioned, a current is sourced from the compactor 140 to the cart 32 to recharge the batteries 80. In FIG. 6 an AC/DC converter 84 is shown as being connected between coil 82 and the battery. AC/DC converter 84 converts the AC signal developed across coil 82 into a DC signal that charge the batteries 80.

An I/O line from processor 74 is shown connected to a modulator/demodulator 88. The modulator/demodulator 88 is shown connected to coil 90. Coil 90 is connected to modulator/demodulator 88 to both receive RF signals from and forward RF signals to the modulator/demodulator. As disclosed below, when cart 32 is mated to compactor 140, data are inductively exchanged between the cart processor 74 and a complementary processor 188 internal to the compactor over the modulator/demodulator 88 and coil 90.

Figure 7A:
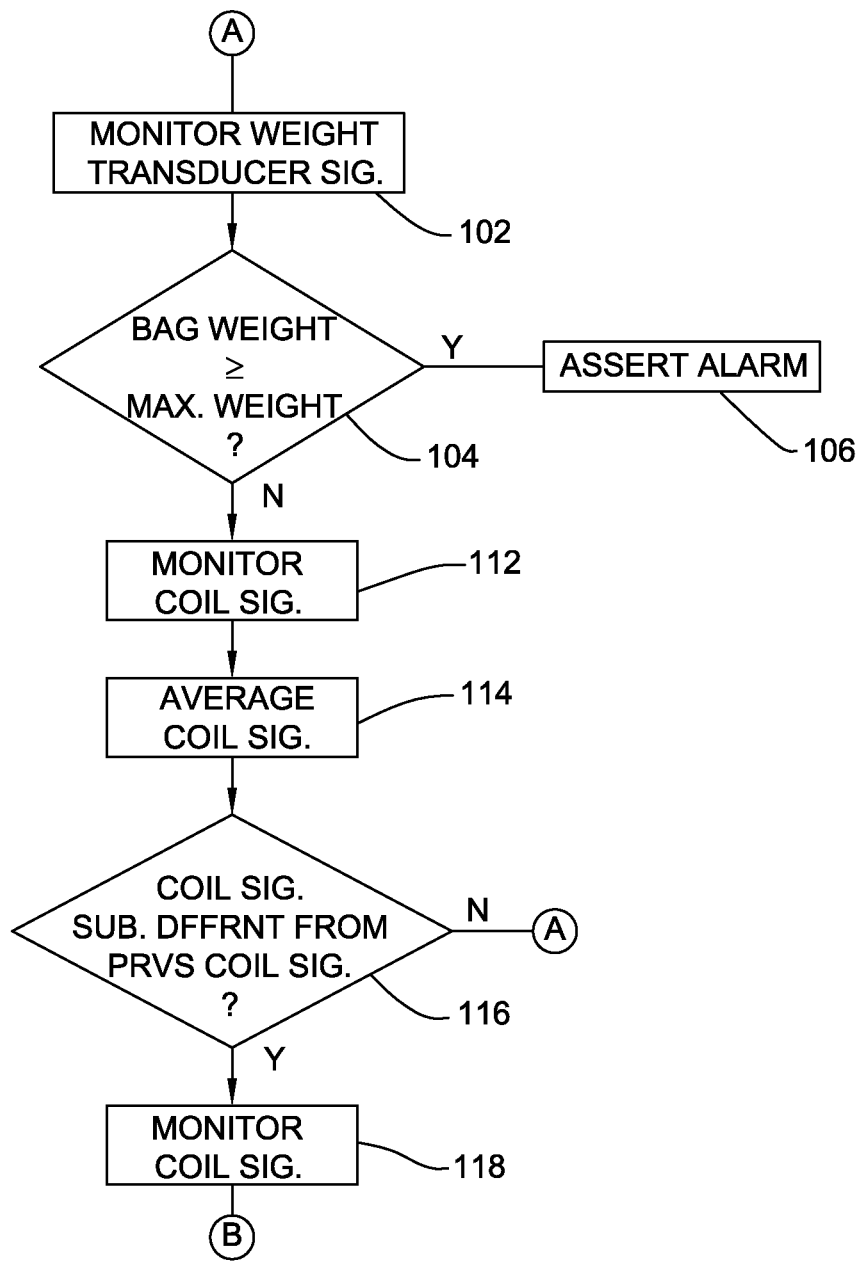
FIGS. 7A and 7B collectively form a flow chart of the evaluations performed by the cart of this invention when a bag is in position and waste articles are being deposited in the bag.
Figure 7B:
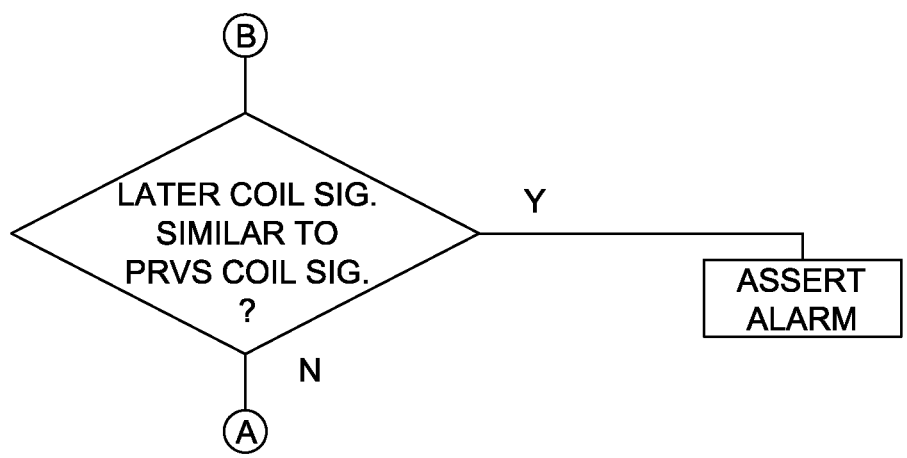

Processor 74 primary function is to monitor the signals output by transducer 56 and coil 72. The signal output by transducer 56 is related to the weight of the material contained in bag 44. When the cart 32 is in use, the processor 74 continually monitors the transducer output signal, step 102 of FIG. 7. Processor 74 compares this signal level to a reference signal level representative of a preferred maximum weight for the bag 44 and its contents, steps 104. In the event the comparison of step 104 indicates that the bag and its contents are above the preferred maximum weight, processor 74, in step 106, asserts an alarm. This alarm may be asserted by actuating the enunciator integral with the display. Alternatively, the alarm is the actuation of a specific light 79 or series of lights.

Processor 74 also monitors the signal that develops across coil 66 to determine if there is rapid change in the signal followed by a return to its initial level. Step 112 of FIG. 7, represents the continual monitoring of the signal from coil 66. In some versions of the invention, this signal is averaged over a period not exceeding one second to obtain a running average, step 114. In a step 116 the actual signal is compared to a preceding signal level. In some versions of the invention, this comparison may be to a signal previously captured 10 to 1000 msec before the signal under review was captured. In other versions of this invention, this comparison is to the previously calculated average signal for the 250 to 1000 msec period immediately preceding the occurrence of the signal under review. The comparison of step 116 may indicate there is not substantial difference in signal levels, the new signal is between 50 and 200% of the level of the prior signal If the comparison of step 116 indicates that there was a substantial change in signal level, such change may be due to the fact that the magnetic field between coils 66 and 72 was momentarily disrupted by the passage of metal instrument between the coils and into the bag. The change in the magnetic field may alternatively be due to the fact that either the cart was positioned adjacent a piece of metal equipment or the placement of such equipment near the cart.

Accordingly, the processor 74 performs an additional evaluation to determine the likely cause of the change in signal level from coil 72. Specifically, if the evaluation of step 116 is positive, the processor continues to monitor the signal level across the coil 72, step 118. This signal may be averaged. Such averaging would be for the same period in which averaging occurs during step 114. Then, in a step 120, this later-averaged signal is compared to the signal under review. If this comparison indicates that the new average signal is similar to the base signal, processor 74 interprets the momentary variation from this signal as being caused by a piece of metal passing between coils 65 and 66. In this event, in step 122 processor actuates display 78 to cause an appropriate alarm to be asserted. This alarm may take the form of the actuation of the enunciator and/or the actuation of a specific one of the lights 79. This alarm is different from the alarm asserted in step 106. This is to provide an indication that a piece of metal may have been placed in the bag 44 attached to cart 32.

Medical personnel use this alarm as a cue to investigate the contents of the bag to determine if the metal-containing article just placed in was an actual waste article or reusable article that should be retrieved.

Alternatively, the comparison may indicate that there is an appreciable difference between the initial signal level and the most recently generated signal level. Processor 74 interprets this test result as indicating the strength of the signal developed across coil 66 is changing because of an event that caused the characteristics of the steady state magnetic field between coils 65 and 66 to change. This change may be due to the repositioning of the cart 32 relative to other metal objects in the room. Alternatively, the change may be due to the emission of an EM field by a surgical instrument.

In the event there change in signal level is due to these changes in environment in which the cart is located, (as opposed to a piece of metal being passed into the bag 44,) processor 74 continues to rexecute steps 102, 104, 112, 114 and 116.

Returning to step 116, the evaluation performed by this step may not indicate there was a significant change in signals between the signal under test and the immediate past signal. In such event, steps 102, 104, 112,114 and 116 are continually reexcuted.

Figure 8:
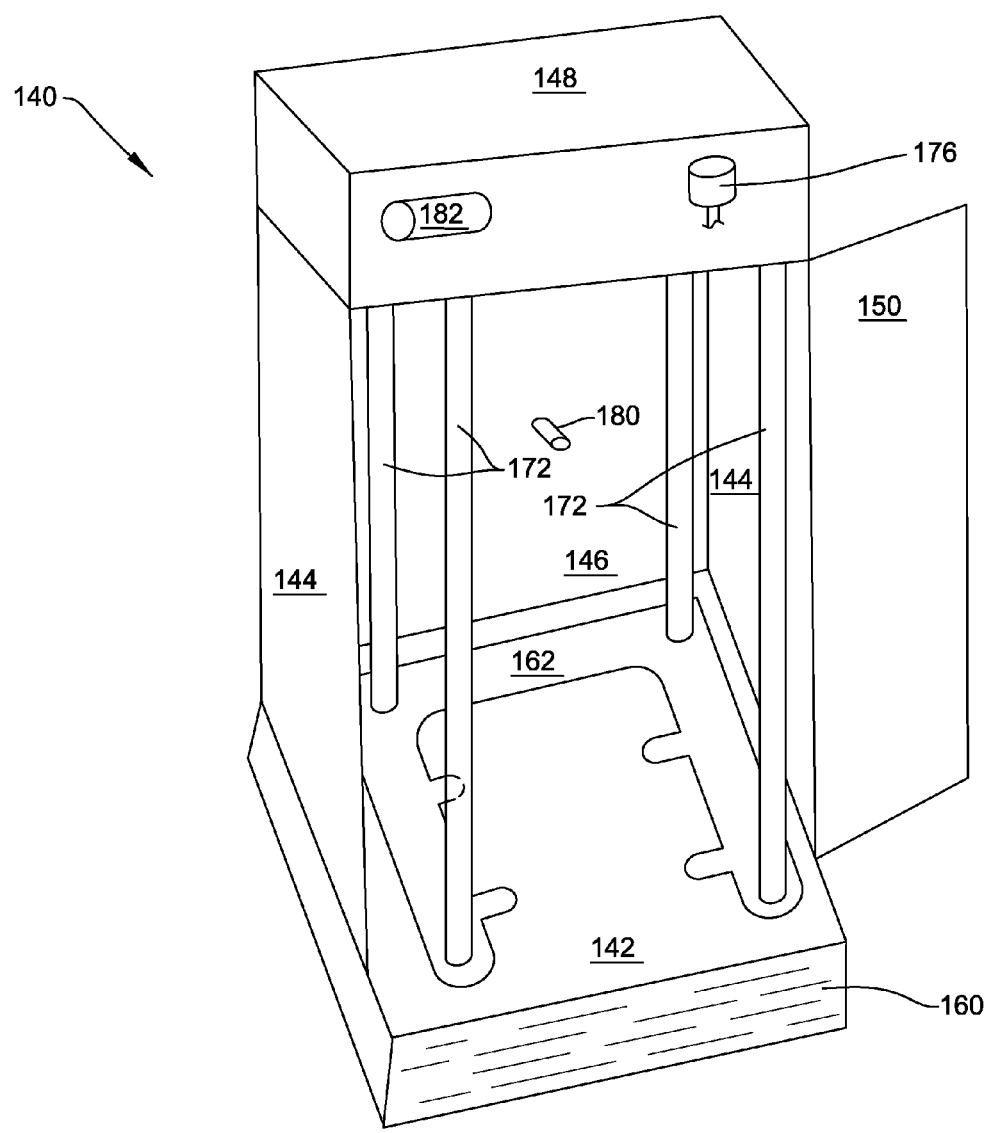
FIG. 8 is a perspective view of a compactor of the system of this invention.

System 30 of this invention also includes compactor 140 now generally described by reference to FIG. 8. Compactor 140 includes a base plate 142, from which two side walls 144 and a rear wall 146 extend. The side walls 144 and rear wall 146 support a head unit 148 above the base plate 142. More particularly, there is sufficient separation between the base plate 142 and the head unit 148 that the cart 32 can be placed in the space therebetween.

A door 150 is hingedly attached to one of the side walls 144. The door 150 can be pivoted to be locked to the opposed side wall in order to enclose the cart 32 in the compactor 140.

Figure 10:
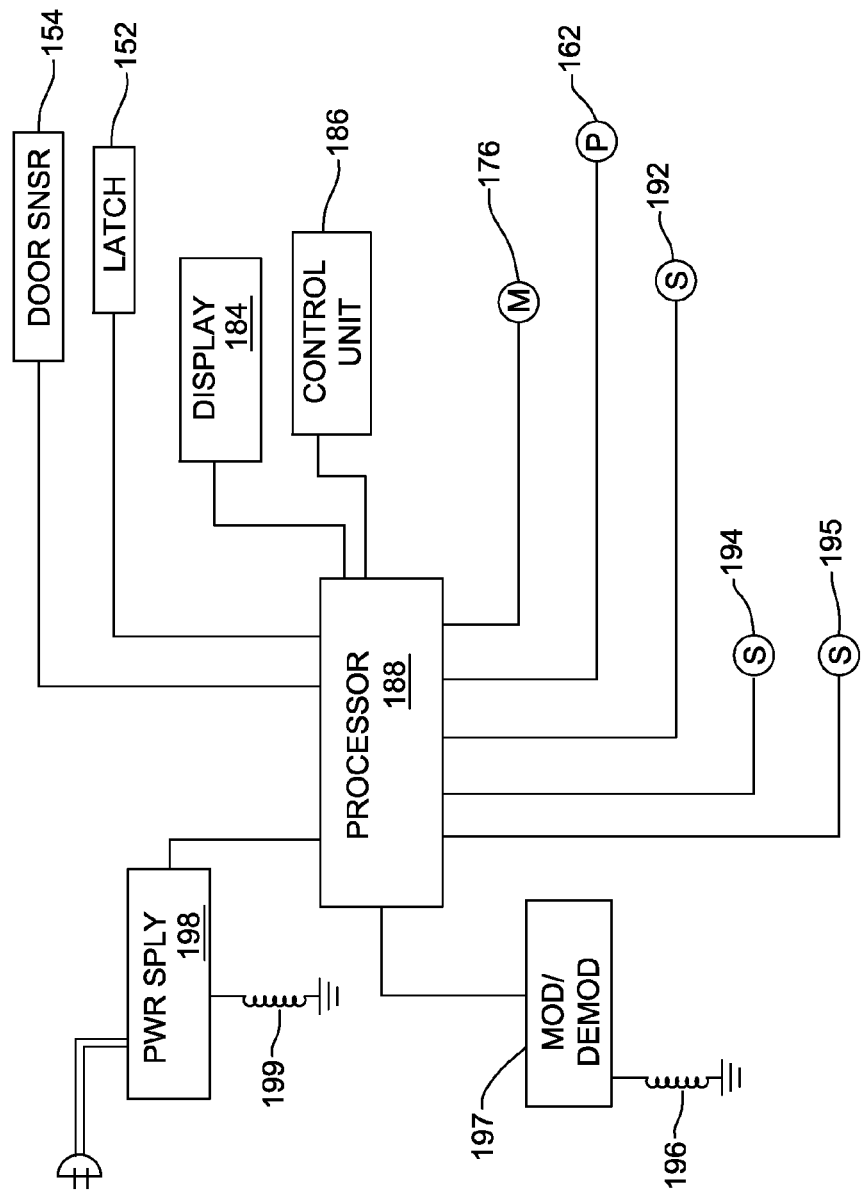
FIG. 10 is a block view of the circuit components integral with the compactor.

Shown as a block diagram component in FIG. 10 is the electronically actuated latch 152 that holds the door in the lock state. This latch may be solenoid type device. Also shown in FIG. 10 is the sensor 154 that is used to monitor whether or not the door 150 is in the closed state. Sensor 154 may be a contact type switch. Alternatively, sensor 154 may be a Hall effect sensor. In versions of the invention wherein sensor 154 is a Hall effect sensor, a complementary magnet is mounted in the door 150. The magnet is positioned so that when the door is placed in the closed state, the magnet is adjacent the sensor 154.

Figure 9:
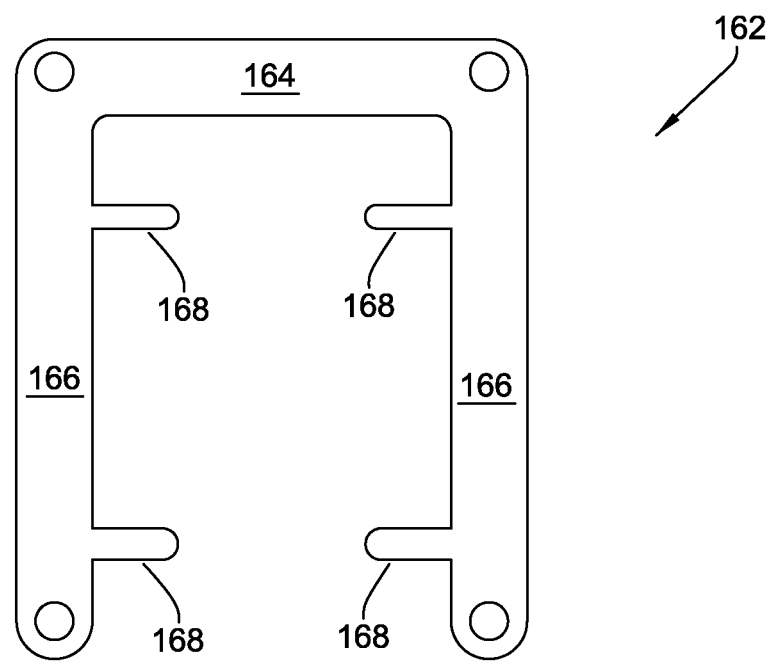
FIG. 9 is a plan view of the lift plate internal to the compactor.

Compactor base plate 142 is a generally planar structure. The forward end of the base plate 142, the end that faces outwardly from the open end of the compactor 140, is formed to have a ramp 160. Ramp 160 angles downwardly to the surface on which the compactor 140 rests. Ramp 160 thus functions as the surface upon which one can roll the cart 32 into the compactor 140. Inside the compactor 140, a lift frame 162 rests on the base plate 142. More particularly, lift frame 162 is seated in a recess in the base plate 142. Collectively, the base plate 142 and lift frame 162 are shaped so that when the lift frame is seated in the base plate recess, the outer surface of the lift frame is flush with the outer surface of the base plate. Lift frame 162, best seen in FIG. 9, is in the form of a three-sided structure; there is a center section 164 from which two arms 166 extend in parallel. Lift frame 162 is dimensioned so that the distance between arms 166 is greater than the width of the cart base 34.

Two fingers 168 extend inwardly from each arm 164. Each finger 168 is in line with a finger 168 that extends inwardly from the opposed arm 164. Collectively the fingers 168 are positioned so that when the cart 32 is placed in the compactor 140, each finger is located below a separate one of the notches 50 defined by the cart base center panel 48.

Four lift screws 172 extend vertically through the compactor 140, from the base plate 142 into the head unit 148. More particularly, each lift screw 172 is rotatably mounted to both the base plate 142 and head unit 148. Each lift screw 172 extends through the lift frame 162. More particularly, the lift screws 172 are arranged so that one lift screw extends through the forward end of each arm and one lift screw extends out of each corner where the arm 166 extends from the center section 162. While not illustrated, it should be appreciated that each lift screw 172 extends through a boss that is attached to the lift frame 162. Each boss extends downwardly from the underside of the frame around the opening in the frame through which the lift screw extends. The inner wall of each boss is threaded so that boss engages the lift screw.

A motor 176 is disposed in the head unit for rotating the lift screws 172. While not illustrated, it should be understood that there is a drive train connected between the output shaft of the motor 176 and the lift screws 172. The drive train is of the type that ensures that when the motor 176 is actuated, each lift screw rotates the same amount. The drive train may consist of a chain that engages gears associated with each of the lift screws and the motor 176. This drive train includes a tensioner that presses against the chain to eliminate slack.

A tube-shaped suction fitting 180 extends forward from the center of the compactor rear wall 146. Suction is drawn through fitting 180 from a pump 182. In FIG. 8, pump 182 is shown as being disposed in compactor head unit 148. This placement should not be interpreted as limiting. Also, it should be understood that the suction fitting, if rigid, may be attached to a rail that allows the fitting to move vertically. If the suction fitting is not attached to a rail, the fitting may be attached to hose, again, to allow the fitting to move vertically.

Compactor 140 also includes a display 184 represented as a block component in the block diagram of FIG. 10. The display 184, in addition to including visual indicia that present information about the operation of the compactor 140 may include an audible alarm. A control unit, represented by block 186, includes the manually actuated members that allow personnel to regulate operation of the compactor 140. In some versions of the invention, display 184 is a touch screen. Thus, the display functions as the module from which information regarding the operation of the compactor is presented and through which commands to control the compactor are entered.

A control processor 188 regulates operation of the compactor 140, namely, motor 176 and vacuum pump 162. The locked/release state of the latch 152 that holds the door closed in also set by the processor 188. Processor 188 receives commands that are entered through the control unit 186. The processor 188 also causes information about the operation and state of the compactor 140 to be presented on display 184.

Processor 188 also receives signals from the sensors built into the compactor 140. These sensors include the previously discussed sensor 154 that monitors the open/closed state of the door 150. Another sensor processor 188 receives a signal from is a pressure sensor 192. Pressure sensor 192 is in line with suction fitting 180.

Processor 188 is further connected to receive signals from lift frame position detect sensors 194 and 195. In FIG. 10 only two sensors are shown. In practice there are sufficient sensors so that processor 188 can determine both when the lift frame has reached its lower and upper limits of travel and a number of points therebetween. If the lift frame sensors consist of contact switches, the switches may be placed apart every 10 to 20 cm. Alternatively, the lift frame sensors may be Hall effect sensors. In this version of the invention, a magnet is mounted to the lift frame. Also in this version of the invention, processor 188, based on the relative strengths of the signals, or a logic tree, is able to determine the position of the lift frame when between the sensors.

Also shown in FIG. 10 is a coil 196. Coil 196 is positioned so that when the cart 32 is seated in the compactor 140, coils 90 and 196 are able to inductively exchange signals. A modulator/demodulator 197 is connected between coil 196 and processor 188. Modulator/demodulator 197 is capable of converting the signals received by coil 196 into signals that can be read by the processor 188. Modulator/demodulator 197 also modulates signals written out by the processor so they can be emitted by coil 197.

A power supply 198 that converts the line signal into signals that can be used to power the various components internal to the compactor 140 is also shown in FIG. 10. For simplicity, only a connection to processor 188 is shown. It is clear that the power supply outputs energization signals to the other components of the compactor 198. Also shown connected to power supply 198 is a coil 199. Coil 199 is positioned so that, when cart 32 is seated in the compactor 140, power signals can be inductively transferred from coil 199 to cart coil 82.

Figure 11:
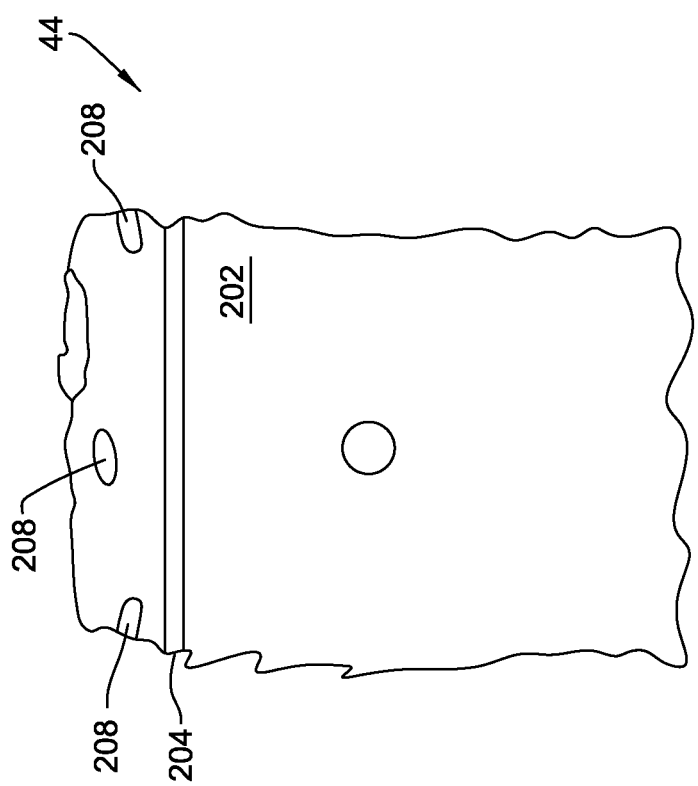
FIG. 11 depicts the bag of this invention.

The bag 44 of this invention, now described by reference to FIG. 11, is formed from a plastic that forms an air tight barrier. Plastics from which bag 44 can be formed include polyethylene, polypropylene or nylon. The bag is formed to have two opposed body panels 202, here seen in FIG. 11. The bottom and side edges of the body panels 202 are sealed together. A air-tight seal assembly 204 is disposed along the opposed side edges of the body panels. One such seal assembly can be the tongue-in-groove wherein the tongue is formed on one strip of semi-rigid (bendable) plastic and the rails that define the groove are formed on a second strip. Alternatively a layer of adhesive material that is normally covered by tape can form the air-tight assembly 204.

Bag 44 is further formed so that above seal 204 four hand holds 208 (two shown) are formed in the bag. Each hand hold 208 is shaped to fit over one of the tabs 42 integral with the cart frame 40. Bag 44 is further shaped so that when the bag is fitted in the frame, the tops of the panels 202 can be rolled over the inner and top surfaces of the frame 40, and partially around the outer surfaces, so that each frame tab 42 can fit in a separate hand hold 208.

Figure 12:
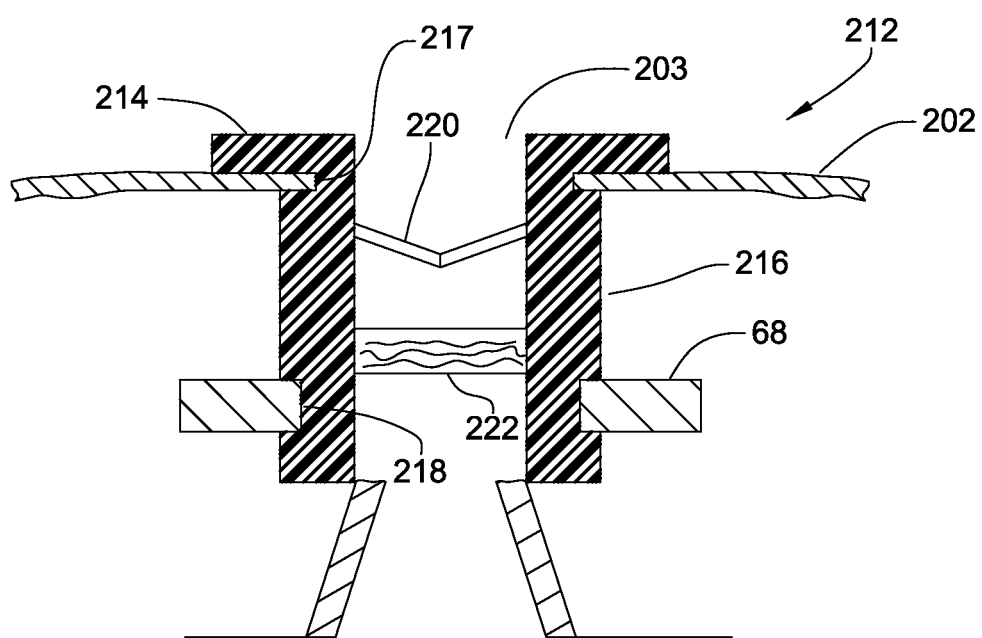
FIG. 12 is a cross sectional view of the valve integral with the bag, wherein the valve is seated in the cart saddle and the compactor suction fitting is positioned to mate with the valve.

A valve 212 is disposed in one of the bag body panels. Generally, the valve 212 is positioned so that when the bag is fitted to the cart, the valve can be seated in the cart saddle 68. As seen in FIG. 12, valve 212 has a body 216 formed of a compressible rubber that is generally tube-shaped. The inner end of the valve body 216, the end disposed inside the bag 44, is formed to have a lip 214 with a larger outer diameter than the rest of the body. Immediately forward of lip 214, the valve body is formed to define an annular groove 217. When the bag 44 is assembled the plastic forming the body panel 202 from which the valve extends is seated in the groove 217. The valve body is secured to panel 202 to ensure an air tight seal between these components. Immediately rearward of the forward end of the valve body 212 there is a second annular groove, groove 218. Groove 218 has a width that allows the cart saddle 68 to be seated in the groove.

Inside the valve body there is a valve element 220, represented by two flaps. The valve element is a one-way valve that only allows flow out of the bag. Also disposed in the center bore of the valve body is a filter element 222. Filter element 222 is capable of trapping particulates and aerosolized liquids.

Cart 32 of the system 30 of this invention is prepared for use by fitting a bag 44 to the cart. The bag is placed within the cart frame so that the body panel to which the valve 212 is attached is below the front web 60. The top of the bag 44 is wrapped over the inner and top surfaces 57 and 59, respectively, of the adjacent webs 60, 62 or 64. The bag is also wrapped at least partially over the web outer surfaces 61. The top of the bag is positioned over the outer surface 61 of the webs so that each one of the web tabs 42 seats in a separate hand hold opening 208. The valve 212 is positioned in the saddle 68.

Immediately prior to the procedure, the cart 32 is actuated. This actuation means that the signal generator 76 is turned on (cart control switches connected to the processor not shown) and the processor 74 actively monitors the signal across coil 66 and the pressure sensed by transducer 56. During the medical/surgical procedure, waste is placed in the bag in a conventional manner.

During the course of the procedure metal objects may be placed in the bag. The transit of such objects between coils 65 and 66 momentarily disrupts the magnetic field between the coils. As discussed above with respect to FIGS. 7A and 7B, this momentary change in signal across coil 72 is detected by processor 74. If the change is detected, processor 74 interprets it as indication that metal has entered the bag 44. Accordingly, per step 106, an alarm is asserted. This alarm provides the medical/surgical personnel with the notice that metal has entered the bag. The alarm thus serves as a cue so that these personnel can verify that the article disposed of was not a reusable device that was inadvertently discarded. If the investigation indicates the article was inadvertently discarded, it can then be promptly retrieved before addition waste is piled on top of it.

During the course of the procedure, the contents of the bag increase. Processor 74, per the steps of FIG. 7A also monitors the weight of the bag as indicated by the signal from transducer 56. If the comparison of step 104 indicates that the weight of the material in the cart is reaching its limit, alarm assertion step 106 is executed. This gives the personnel notice that it is now appropriate to substitute bags or provide a back-up cart with an empty bag.

Eventually, there is a point in the procedure at which one or more of the bags 44 are ready for closure. For a particular bag this may be because, as a result of the execution of step 104 it is determined that the bag is full. Alternatively, it may be that the actual medical/surgical procedure is complete and the bag, while not full, is ready for short term storage and transport.

The process of preparing the bag 44 for storage and transport begins with the closure of the seal 204. This step is performed with the bag remaining in the cart 32. As part of this step, it often necessary to unwrap the bag flaps, the sections of the bag above the seal 204, from the cart frame. However, during this step, the bag valve 212 remains mounted in the cart saddle 68.

Compactor 140 is then used to reduce the volume of the bag 44 and its contents. This process, now described by reference to the flow chart of FIGS. 13A through 13C, begins with step 230, the rolling of the cart 32 in the compactor 140. Specifically, the cart 32 is placed in the compactor 140 so that the front web 60 faces the forward facing surface of the compactor rear wall 146. As a result of the alignment of the cart saddle 68, the bag valve 212 in the saddle and the compactor suction fitting 180, this positioning of the cart results in the valve 212 aligning with the suction fitting 180. Owing to the relative dimensioning of the valve body 216 and the suction fitting 180 the movement of the cart towards compactor rear wall 146 results in the fitting seating inside center bore of the valve. Owing to the tapered shape of the suction fitting 180 and the elastomeric nature of the material from which the valve body 216 is formed, the continued forward movement of the cart 32 results in the valve body 216 sealing over the suction fitting 180. A further sub-step in the preparation of the bag for compaction is the closing of door 150 so as to enclose the cart 32 in the compactor 140. This sub-step is also part of step 230.

Step 232 represents the actuation of the compactor 140. The user performs this activity by depressing the appropriate button on the control unit 186. In immediate response to this activity, and depicted as part of step, the control processor 188 first reviews the state of the signal from sensor 154 to determine if the door 150 is closed. If the door is not closed, the processor 188 actuates an appropriate alarm, (sub-step not shown). If door 150 is closed, processor 188 sets latch 152 to the locked state. This action prevents the door 150 from being opened during the compaction process.

Compactor control processor 188 then reads at least some of the data stored in the cart processor 74. In particular, the compactor control processor 188 reads from cart processor 74 data representative of the weight of the bag 44 and the waste articles contained therein, step 234. This data read, it should be understood, is through the inductive transfer of modulated data signals between cart coil 90 and compactor coil 196.

Based on the weight of the bag and its contents, in a step 236, compactor processor 188 determines the extent the bag and it contents should be compressed. Generally, the higher the weight of the bag and its contents, the less the bag is subjected to compression. In one version of this invention, the result of this analysis is an indication of the height the lift frame 162 is to be lifted above the compactor base plate 142. Therefore, should the bag and its contents be light in weight, step 236, processor 188 determines that that lift frame 162 can be raised a relatively high amount. If the bag weight is relatively high, than the result of step 236 determines that the lift frame can only be raised to a relatively low height.

Immediately prior to the actual compression of the bag 44, processor 188, in a step 238, actuates suction pump 182 to cause an initial suction to be drawn on the interior of the bag 44. This initial suction is a suction that causes the pressure inside the bag to drop below the ambient air pressure. The suction is clearly at least enough to overcome the force holding valve element 220 closed. As a result of the pressure inside the bag falling to below the ambient atmosphere, the ambient pressure exerts an inward force on the outer surfaces of the bag. This force results in the bag panel collapsing inwardly on the contents of the bag 44.

During step 238, and the subsequent steps in which a suction is drawn, more than air is removed from the bag 44. Aerosol and droplet sized particles of liquid and small bits of matter may also be drawn by the suction toward the compactor 140. This liquid and solid matter may include biologic material including contaminates. Prior to this matter leaving the bag 44, it is trapped by filter element 222.

Once the initial suction is drawn against the bag 44, compactor motor 176 is actuated to start the actual compression process, step 240. The actuation of motor 176 results in the simultaneous rotation of the lift screws 172. The rotation of the lift screws 172 result in the lift plate 162 moving upwardly. Initially, the lift plate fingers 168 simply pass through the notches 50 defined by the cart base center panel 48. Once the lift plate fingers 168 complete this transit, they abut the compression plate 46. As the lift plate 162 continues the upward movement, fingers 168 displace the compression plate 46 in the like direction. This upward movement of the compression plate results in the bag 44 and its contents being compressed between the plate and the underside of the compactor head unit 148.

At this time, and therefore also depicted as part of step 240, pump 182 is actuated to cause a compaction suction to be drawn against the bag 44. This compaction suction may be at or at a slightly higher level (larger pressure drop compared to the ambient atmosphere) than the initial suction. In some versions of this invention, this compaction pressure is maintained throughout the compression cycle.

Figure 13A:
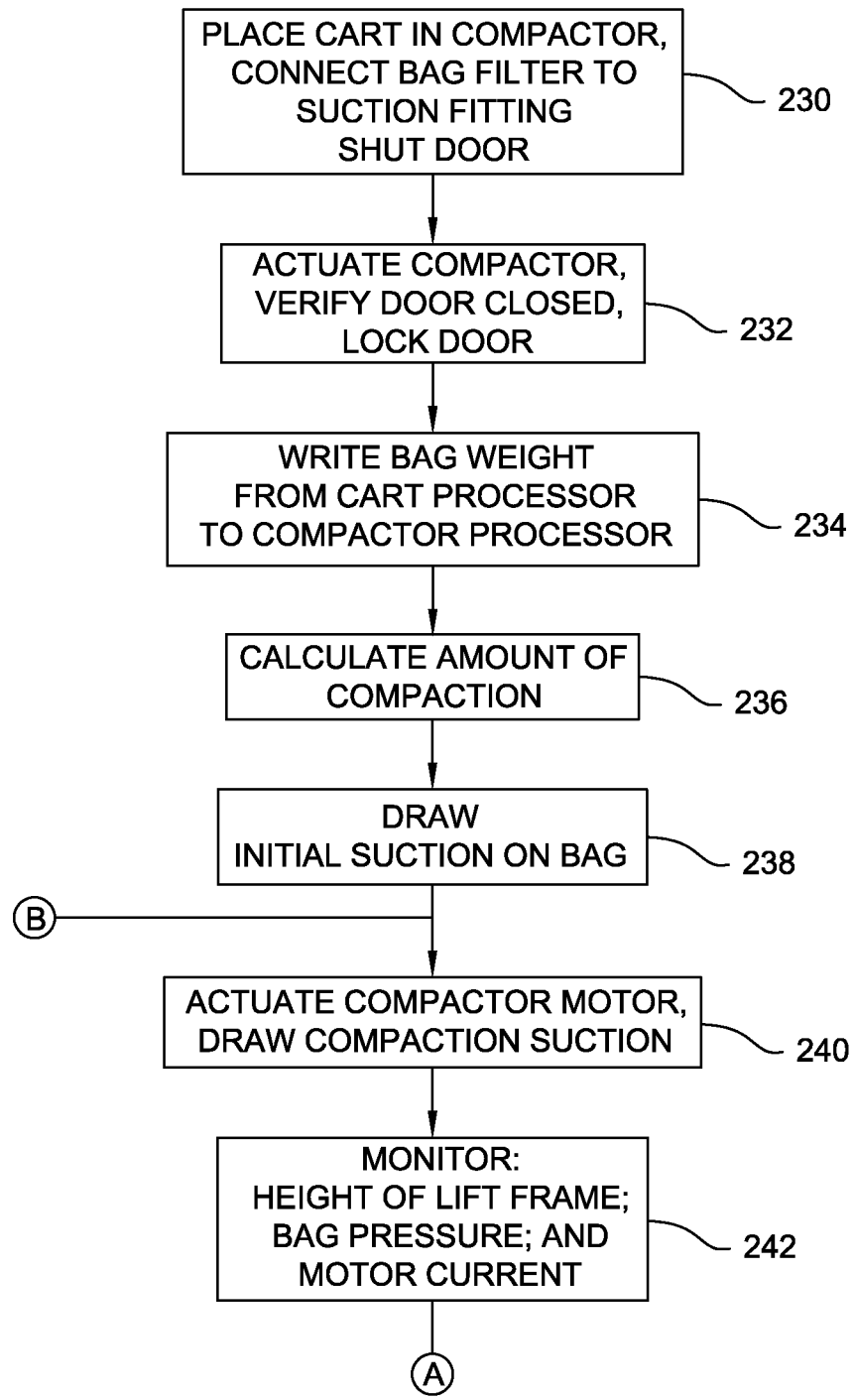
FIGS. 13A-13C collectively form a flow chart of the process steps of the waste compaction process of the system and method of this invention.

Simultaneously with the actuation of motor 176 and the drawing of the compression suction, control processor 188 continually monitors the height of the lift frame 162, the pressure internal to the bag 44 and the current drawn by motor 176. In FIG. 13A, these three processes are shown as a single step 242. Specifically, the signals output by sensors 194 and 195 are monitored to determine the height of the lift frame 162. The output signal from sensor 192 is monitored to determine the pressure internal to the bag 44. Motor current can be monitored by measuring the voltage across a resistor tied between the motor windings and ground (motor windings and resistor not identified).

Upon determining the height of the lift frame 162, control processor 188 compares this height to the calculated height from step 236, to which the frame should rise, step 248.

If the actual height is equal to or greater than the calculated height, the control processor 188 recognizes the compactor 140 as being in a state which the compactor has fully compressed the contents of bag 44. If processor 188 makes this determination, the processor, in step 250, deactivates motor 176. This causes the compression of the bag 44 and its contents to cease. Once motor 176 is deactivated, pump 162 is reset to draw a final suction on the bag. The vacuum drawn in step 251 is greater than the vacuum previously drawn. (Larger difference between ambient and bag absolute pressures.)

The signal asserted to the latch 152 is reset to allow door 150 to be opened, step 252. Step of opening the door not shown. Once door 150 is open, in a step 254 the bag valve 212 is decoupled from the suction fitting 180. To perform this part of step 254 it may be necessary to vent ambient air into the bore of the suction fitting 180. This sub-step is performed by pulling the bag towards the cart leg 38. Valve 212 integral with the bag 44 maintains the vacuum pressure on the bag.

Control processor 188 then presents a message to the user on the display prompting the user to again shut door 150. Once door 150 is so shut, processor 188 again asserts a signal to latch 154 that results in the latching of the door shut. Collectively, the above steps are shown as a reclose door step 255.

Upon the reclosing of the door 150, control processor 188 reactuates the compressor motor 176, step 256. In step 256, motor 176 is actuated to cause the rotation of the lift screws 172 that results in the lowering of the compression plate 46. The compression plate 46, with the bag 44 of compressed waste thereon, is lowered, until the signal from sensors 194 and 195 indicate that lift frame has returned to its lowest position. As an inherent part of this process of the return of the lift plate to its initial state, the compression plate and bag of compressed waste seat on the cart base 34. Collectively each of these sub-steps is part of step 256.

After the bag 44 of compressed waste is disposed on the cart base 256. Control processor 188 again unlocks door 150. The door 150 is then opened. Cart 32, with the bag of compressed waste, is then removed from the compactor 140. At this time, the cart can be used to wheel the bag of compressed waste to the transfer station where it is stored prior to transport for offsite disposition, step 260. Collectively, this second unlocking of door 150, the opening of the door and removal of the cart 32 are shown as step 258. The person responsible for transferring the bag 44 can use hand holds 208 to move the bag.

From the evaluation of step 248, it may be determined that the lift frame 162 has not risen to the designated height. If the compactor 140 is in this state, processor 188, in a step 262, compares the current drawn by compactor motor 176 to a maximum current level. The current drawn by the motor 176 is directly related to the force the motor exerts on the compression assembly. Therefore, the comparison of step 262 is performed to evaluate if the motor is exerting a pre-defined maximum amount of force.

If the evaluation of step 262, is positive, a maximum amount of force is being exerted, control processor 188 again recognizes the compactor as being in a state in which compaction should be considered completed. The control processor 188 then causes the previously described steps 250-260.

If the comparison of step 262 does not reveal that the motor is using above the maximum amount of force to compress bag 44 and its contents, the bag pressure is compared to a maximum pressure, step 264. This comparison is performed to determine if a sharp object in the bag has inadvertently caused a tear in the bag. During compression cycles during which bag integrity is maintained, the atmospheric pressure within the bag will remain low. However, in the event of a tear, the pressure internal to the bag will approach, if not equal, the absolute pressure of the ambient environment. Accordingly, the detection in step 264 of a pressure above a threshold pressure is interpreted by the processor 188 as an indication that the integrity of the bag has been breached.

If processor 188 determines that bag integrity has been breached, the processor 188 deactivates the motor 176 to stop the compression process, step 266. Step 266 is performed first to minimize the possibility that further compression could result in additional tearing of the bag 44. An alarm is actuated, step 268, to give the user notice of the potential state of the bag. Suction is then terminated and the door unlocked and opened, step 270. Previously described steps 254-260 are then executed so that cart and bag can be removed from the compactor.

Figure 13B:
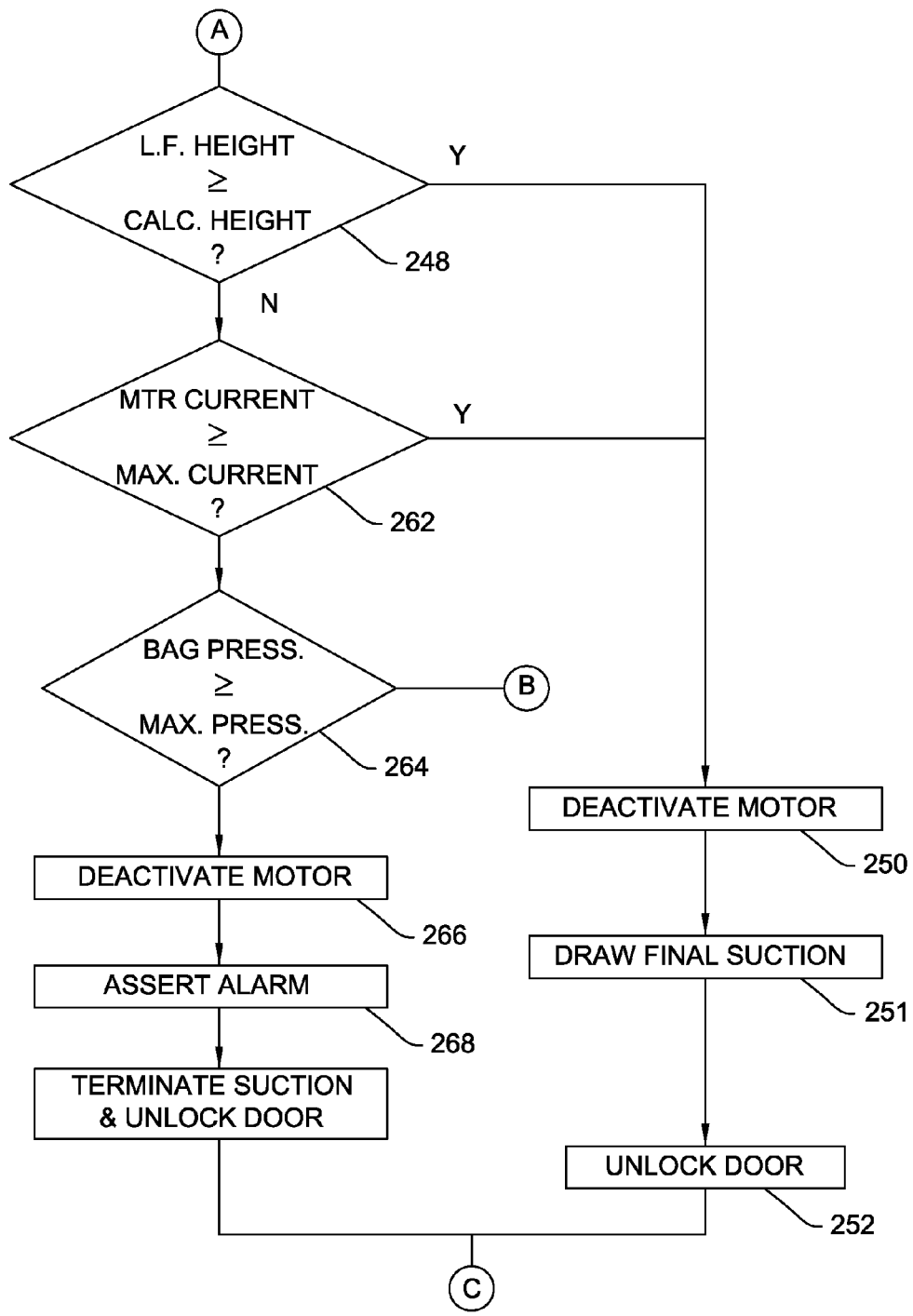
Figure 13C:
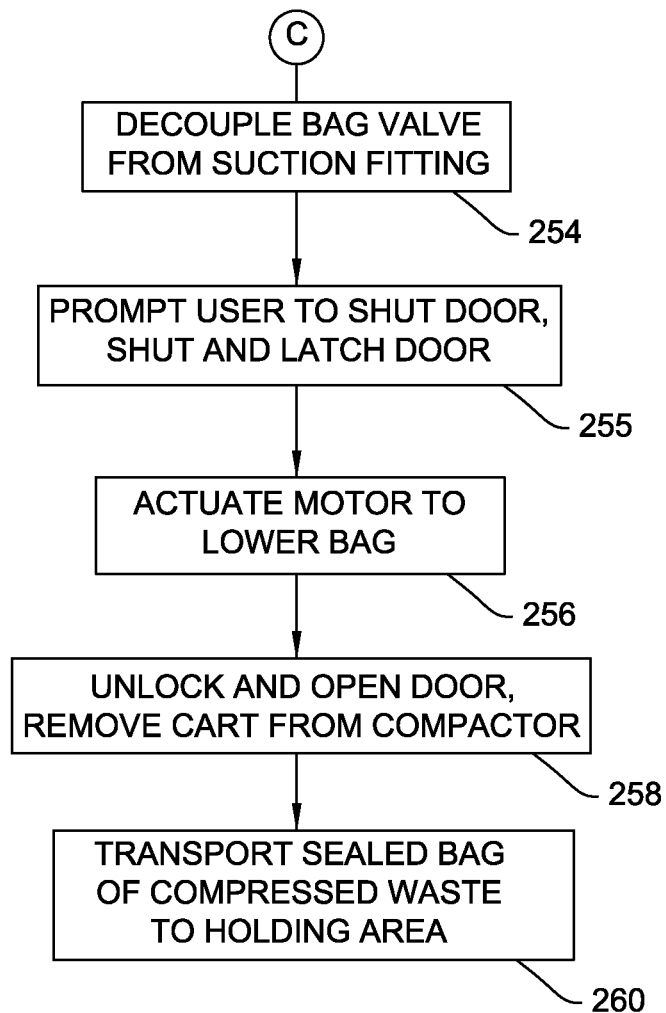

If the evaluation of step 264 does not indicate that there has been any bag tearing, control processor 188 allows the compression process to continue. In FIGS. 13A and 13B, this is represented as the loop from step 264 back to step 240.

Also, while not illustrated as an explicit step, during the time the cart 32 is in the compactor 140, the compactor power supply 198 supplies a charging current to the cart batteries 80. This power is supplied as a result of the inductive transfer of a charging signal from compactor coil 190 to cart coil 82. The AC/DC converter 84 internal to the cart outputs the signal sourced by power supply 198 to the cart batteries 80.

System 30 of this invention provides a means for receiving and temporarily storing in compressed form, waste that is generated during a medical/surgical procedure. The cart 32 of this invention is configured to assert an alarm in the event a metal object is thrown in the attached bag 44. This alarm provides a notice that a reusable medical device may have inadvertently been discarded. Personal can then investigate to determine if this event occurred, and, if it did, to retrieve the device from the bag before it is covered with other waste.

Cart 32 of this invention also asserts an alarm when the contents of the bag approach a maximum weight. Personnel then have the opportunity to replace the bag 44 before its weight makes it difficult to handle.

Once a bag 44 is ready for compaction, seal 204, provides an easy means to close the bag. This prevents, the odors generates by the contents of the bag from being further released into the surrounding environment.

Prior to the start of the compaction, a suction is drawn on the bag 44. This suction draws the bag panels inwardly, away from the side and rear panels and door of the compactor and the cart leg 38. This inward displacement of the bag panels reduces the likelihood that the bag could scrape along these surfaces and rip.

Post compaction an additional suction draw reduces the size of the bag and compacted articles contained therein. This compaction reduces the size of the bag and its contents so as to make it easier for manual handling and short term, at facility storage. The reduction in bulk of the bags also further simplifies the transport of the bags to the processing site.

Figure 14:
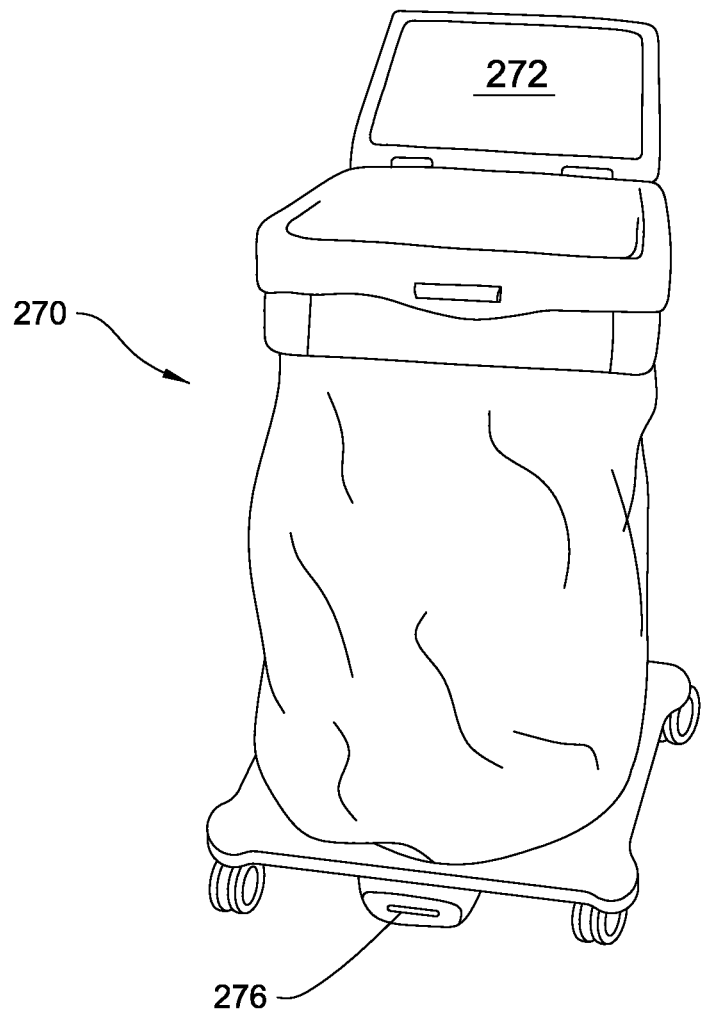
FIG. 14 is a perspective view of an alternative cart of this invention.

FIG. 14 illustrates that a cart 270 of this invention may be provided with a lid 272. While not illustrated, lid 272 can be pivotally attached to the frame from which the bag is suspended. Lid 272 normally covers the bag to minimize the release of odors from the contents of the bag 44. A linkage mechanism (not illustrated) controlled by a foot lever 276 attached to the base of the cart is actuated to pivot the lid 272 open.

In some version of the invention, lid 272 is removably attached to the cart 270. Lid 272 is then removed prior to placement of the cart in the compactor 140. Alternatively, prior to placement of the lid in the compactor, the lid is pivoted to be flat against the leg of the cart prior to placement in the compactor.

Figure 15:
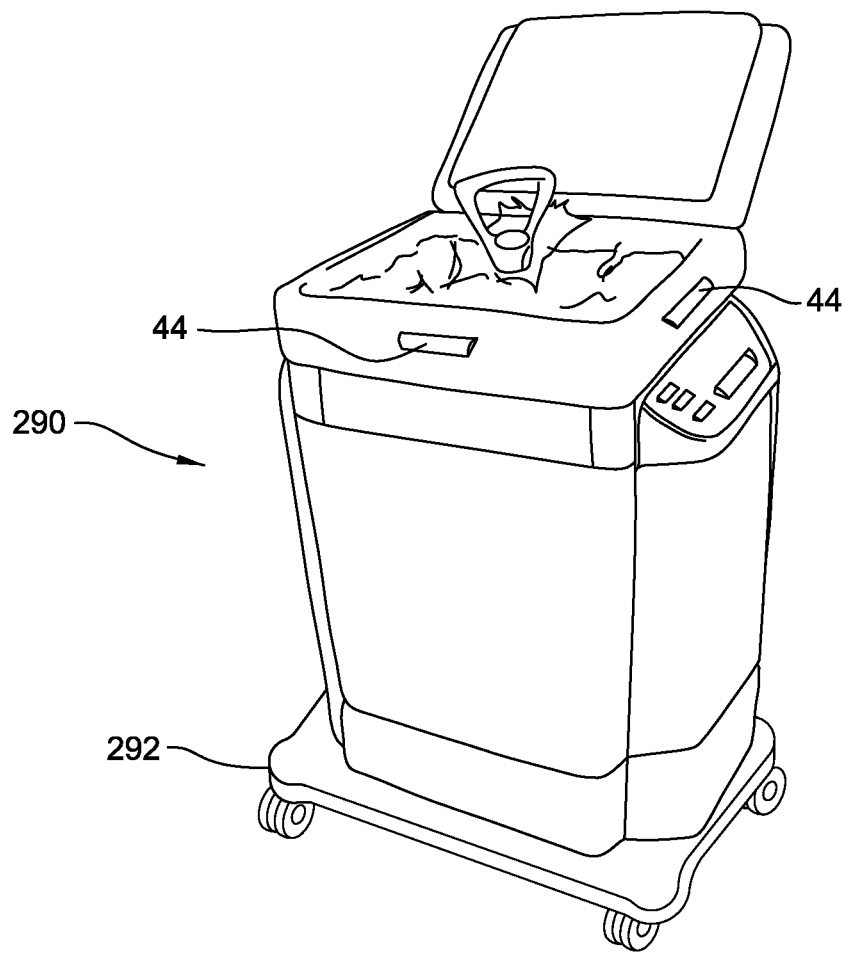
FIG. 15 is a perspective view of a mobile compactor of this invention.

An alternative compactor 290 of this invention is now described by reference to FIG. 15. Compactor 290 includes a base 292 mounted on castors (not illustrated) so that the compactor is its own cart for use in the room where the medical/surgical procedure is performed.

Compactor 290 has front, rear and side walls. Coils similar to coils 65 and 66 are mounted in the top of the front and side walls for metal detection (coils not illustrated). Disposed inside the compactor 290 are a compressor plate and transducer similar to the versions of these components contained in cart 32 (compressor plate and transducer not illustrated). Compactor 290 includes a lift frame (not illustrated) that is located below the compression plate. A drive mechanism, such as lift screws, selectively advances and retracts the compression plate towards and away from the lid.

Figure 16:
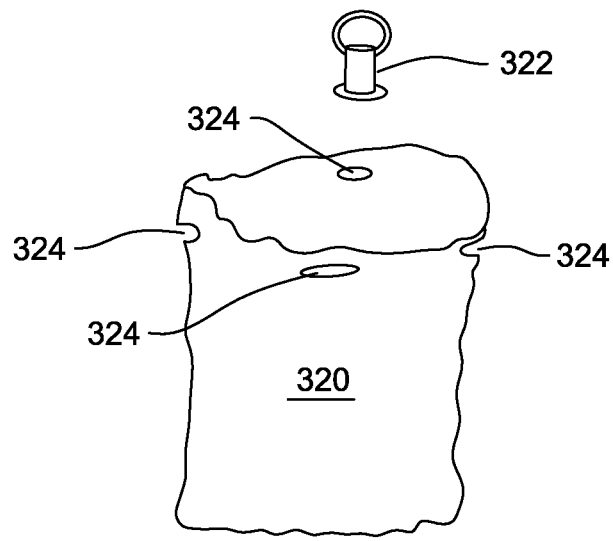
FIG. 16 is an exploded view of an alternative bag of this invention and the filter cartridge fitted to the bag.

FIG. 16 illustrates that bag 320 and valve cartridge 322 that may be used with this version of the invention. Bag 320 is very close to a standard two-panel bag. Four openings 324, (three shown) are formed in the top of the bag 320. The openings 320 are for fitting the bag over the mounting tabs 42 disposed around the top opening into the compactor.

Figure 17:
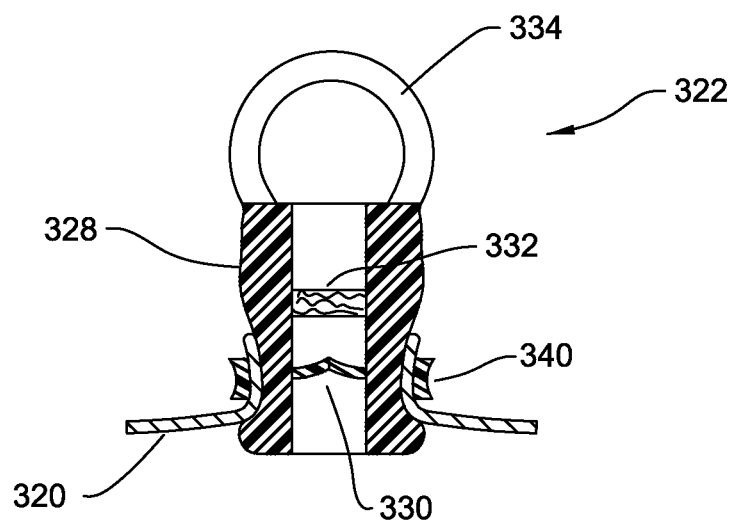
FIG. 17 is a cross sectional view of the filter cartridge of FIG. 16.

Cartridge 322, best seen in FIG. 17, has a tube like body 328. Body 328 is formed from a rubber or plastic that has a slight degree of compressibility. A bore extends axially through the body 328. The outside of the body is formed to have a base with a first diameter, waist that has an outer diameter that tapers inwardly from the base and a head with a diameter that tapers outwardly from the waist. A one-way valve 330 that only allows flow out of the bore is disposed in the body. A filter 332 similar to previously described filter 222 is also disposed in the body bore.

At least one handle 334 is attached to the cartridge body 328. Handle 334 is a loop of flat plastic that extends upwardly from the head of the body. While only one handle 334 is shown, two handles that symmetric around the center axis of the body 328 are typically provided.

When bag 320 and its contents are ready for compression, the bag is unwrapped from the top opening around the compactor 290. Cartridge 322 is placed in the open end of the bag 320. The top of the bag 320 is wrapped around the cartridge body waist. A plastic tie strip 340 or other fastening means is used to hold the bag tight against the cartridge. Owing to the compressible nature of the material forming the outer surface of the cartridge, a tie strip 340 is able to hold the bag to the cartridge so as to produce a substantially air-tight seal. A hose, not illustrated, is connected to the open end of the cartridge body 328. The hose connects the cartridge to the vacuum pump internal to the compactor 290.

Compactor 290 is then used in a manner similar to that in which the first described compactor is used. The lid to the compactor is closed. An initial suction is drawn on the bag. The bag and its contents are compressed while the suction is continually drawn. A final suction may be drawn after the end of the compression process.

An added advantage of this version of the invention is that the unit in which the waste is initially discarded also functions as the unit in which the waste is compressed for short term storage and ease of handling.

Figure 18:
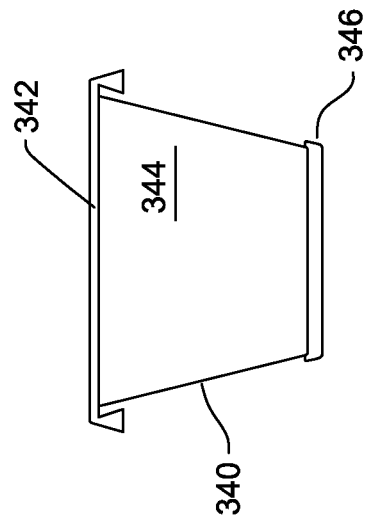
FIG. 18 is a side view of a specimen cup designed for use as part of the system of this invention.

A specimen cup 340 with attached cap 342 designed for use as part of system 30 of this invention is seen in FIG. 18. Specimen cup 340 has a cup shaped body 344. Cap 342 is designed to be snap fitted or screwed on over the open top end of the cup 340. Both the cup body 340 and cap 342 are formed of plastic. A metal base 346 is secured to the underside of cup body 344. The base 346 may be disc-shaped to ensure that when the cup 340 is on a level surface, it remains stable. Metal base 346 is secured to the body such that it does not come into contact with the specimen inside the cup 340.

Specimen cup 340 of this invention is used like a conventional specimen cup; it holds tissue samples extracted for analysis. Owing to the presence of the metal base 346, should this cup 340 be inadvertently placed in the cart 32 or compactor 290, the metal detection circuit will sense this event and an alarm will be asserted. This provides the personnel with the notice needed to prompt retrieval of the cup before such task becomes unduly burdensome.

It should be appreciated that other versions of the system of this invention may have features different from what has been described above. Thus there is no reason that each of the features of the disclosed versions of the invention be in each version of the invention. Likewise the features of the two described versions of the invention may be combined with each other.

Other versions of the invention may have features different from what has been described. Other assemblies may be used to compress the bag and its contents. For example, a scissors-type lift jack may be employed.

Furthermore, other filter assemblies may be used to ensure that the gaseous-state fluid suction-withdrawn from the bag does not result in the discharge of potential contaminates in the ambient environment. Thus, it may be desirable to place a multi-use filter cartridge in the compactor. An advantage of this version of the invention is that it the cost of providing the filter with the bag is eliminated.

The vacuum hose of the second compactor may be used instead of the suction fitting of the first compactor.

In other versions of the invention, fewer process steps than what is described may executed during the actual compression process. Alternative process sequences are also possible. Thus the monitoring of the metal detecting sensor integral with the cart may occur more frequently than the monitoring of the weight of the bag attached to the cart.

The bag may have different features than what has been described. Thus, as mentioned above, in some configurations of the system of this invention, each bag may not have its own filter.

The metal member attached to the specimen cup to ensure its detection by the cart or compactor sensing circuit may be located at a position other than on the base of the cup. Thus, the metal could be in the form of a ring or band of metal that partially or completely circumferentially extends around the cup body.

Therefore, it is an object of the appended claims to cover all such variations and modifications that come within the true spirit and scope of this invention.

What is claimed is:

1. A method of collecting and compacting waste generated during a medical or surgical procedure, said method including the steps of:
    fitting a bag with an opening to a cart, the cart having a plate that is moveably mounted to the cart wherein, in said fitting of the bag, the bag is disposed adjacent the plate and wherein the bag has a one way valve through which air can be discharged from the bag and that blocks air flow into the bag;
    collecting waste generated during a medical or surgical procedure by placing the waste in the bag through the opening;
    closing the bag opening;
    while the bag is on the cart, moving the cart and bag to a compactor; and
    after said step of closing the bag and while the bag remains on the cart, compressing the bag wherein said compression step is performed by an actuator integral with said compactor moving the cart plate towards a static location on the compactor and wherein, as a result of said compression step, air within the bag is discharged through the one way valve.

2. The method of collecting and compacting waste generated during a medical or surgical procedure of claim 1, wherein a further step of compressing the bag is performed by drawing a suction from the bag through the one way valve.

3. The method of collecting and compacting waste generated during a medical or surgical procedure of claim 1, further including the step of filtering the air discharged from the bag through the one way valve.

4. The method of collecting and compacting waste generated during a medical or surgical procedure of claim 3, wherein said step of filtering the air is performed with a filter attached to the bag that is in line with the one way valve.

5. The method of collecting and compacting waste generated during a medical or surgical procedure of claim 1, wherein, in said compression step, the cart plate is moved upwardly.

6. The method of collecting and compacting waste generated during a medical or surgical procedure of claim 1, wherein, during said step of closing the bag opening, the one way valve is seated in the bag opening and the bag is closed around the one way valve.

7. The method of collecting and compacting waste generated during a medical or surgical procedure of claim 1, wherein:
   during said step of compacting the bag, monitoring the pressure of the bag;
   comparing the pressure of the bag to a target pressure to determine if the bag is torn; and
   if, as a result of said pressure comparison step, it is determined that the bag is torn, terminating said step of compressing the bag.

8. The method of collecting and compacting waste generated during a medical or surgical procedure of claim 1, wherein:
   when the bag is fitted to the cart, the bag one way valve is fitted to a saddle attached to the cart;
   as a result of said step of moving the bag and cart to the compactor, the positioning of the cart results in the one way valve engaging a suction fitting integral with the compactor; and
   said step of compressing the bag includes the drawing a vacuum on the interior of the bag by the compactor through the suction fitting and the one way valve.

9. The method of collecting and compacting waste generated during a medical or surgical procedure of claim 1, wherein:
   during said step of collecting the waste generated, with a metal detector mounted to the cart, monitoring items placed in the bag to determine if an item includes metal; and
   if, in said metal determining step, it is determined that the item placed in the bag includes metal, actuating an alarm.

10. The method of collecting and compacting waste generated during a medical or surgical procedure of claim 1, wherein:
    prior to said step of compressing the bag, the weight of the bag is determined;
    based on the weight of the bag, determining a maximum extent to which the cart plate should be pressed against the bag; and
    monitoring the extent to which the cart plate is pressed against the bag and determining if the extent to which the plate has been pressed is equal to the maximum extent to which the plate should be pressed; and when the plate has been pressed against the bag to the maximum extent, terminating said step of compressing the bag.

11. A method of collecting and compacting waste generated during a medical or surgical procedure, said method including the steps of:
    fitting a bag with an opening to a cart, wherein the bag has a one way valve through which air can be discharged from the bag and that blocks air flow into the bag;
    collecting waste generated during a medical or surgical procedure by placing the waste in the bag through the opening;
    closing the bag opening;
    while the bag is on the cart, moving the cart and bag to a compactor;
    after said step of closing the bag and while the bag remains on the cart, compressing the bag using the compactor so that air within the bag is discharged through the one way valve;
    while performing said compression step, monitoring the pressure of the bag;
    comparing the pressure of the bag to a target pressure to determine if the bag is torn; and
    if, as a result of said pressure comparison step, it is determined that the bag is torn, terminating said step of compressing the bag.

12. The method of collecting and compacting waste generated during a medical or surgical procedure of claim 11, wherein said step of compressing the bag is performed by at least one of: drawing a suction from the bag through the one way valve; or applying a force against the bag to urge a portion of the bag towards a static portion of the compactor.

13. The method of collecting and compacting waste generated during a medical or surgical procedure of claim 11, further including the step of filtering the air discharged from the bag through the one way valve.

14. The method of collecting and compacting waste generated during a medical or surgical procedure of claim 13, wherein said step of filtering the air is performed with a filter attached to the bag that is in line with the one way valve.

15. The method of collecting and compacting waste generated during a medical or surgical procedure of claim 11, wherein, during said step of closing the bag opening, the one way valve is seated in the bag opening and the bag is closed around the one way valve.

16. The method of collecting and compacting waste generated during a medical or surgical procedure of claim 11, wherein:
    when the bag is fitted to the cart the bag one way valve is fitted to a saddle attached to the cart;
    as a result of said step of moving the bag and cart to a compactor, the positioning of the cart results in the one way valve engaging a suction fitting integral with the compactor; and
    said step of compressing the bag includes drawing a vacuum on the interior of the bag by the compactor through the suction fitting and the one way valve.

17. The method of collecting and compacting waste generated during a medical or surgical procedure of claim 11, wherein:
    during said step of collecting the waste generated, with a metal detector mounted to the cart, monitoring items placed in the bag to determine if the item includes metal; and
    if, in said metal determining step, it is determined that the item placed in the bag includes metal, actuating an alarm.

18. A method of collecting and compacting waste generated during a medical or surgical procedure, said method including the steps of:

fitting a bag to cart, the bag having an opening and a one way valve, the valve configured to allow the discharge of air from the bag and to block air flow into the bag, the cart having a saddle;

positioning the bag one way valve so that the valve is attached to the cart saddle;

collecting waste generated during a medical or surgical procedure by placing the waste in the bag through the opening;

closing the bag opening;

while the bag is on the cart, moving the cart and bag to a compactor, the compactor having a suction fitting wherein, as a result of said step of moving the bag and the cart to the compactor, the bag one way valve engages the compactor suction fitting; and after said step of closing the bag and while the bag remains on the cart, compressing the bag wherein said compression step is at least performed by drawing a vacuum on the bag through the compactor suction fitting and the bag one way valve.

19. The method of collecting and compacting waste generated during a medical or surgical procedure of claim 18, wherein a further step of compressing the bag is performed by pressing a plate against said bag.

20. The method of collecting and compacting waste generated during a medical or surgical procedure of claim 18, further including the step of filtering the air discharged from the bag through the one way valve.

21. The method of collecting and compacting waste generated during a medical or surgical procedure of claim 20, wherein said step of filtering the air is performed with a filter attached to the bag that is in line with the one way valve.

22. The method of collecting and compacting waste generated during a medical or surgical procedure of claim 18, wherein, during said step of closing the bag opening, the one way valve is seated in the bag opening and the bag is closed around the one way valve.

23. The method of collecting and compacting waste generated during a medical or surgical procedure of claim 18, wherein:

during said step of collecting the waste generated, with a metal detector mounted to the cart, monitoring items placed in the bag to determine if the item includes metal; and if, in said metal determining step, it is determined that the item placed in the bag includes metal, actuating an alarm attached to the cart.

24. The method of collecting and compacting waste of claim 18, wherein said step of positioning the bag one way valve in the cart saddle is performed prior to said step of collecting the waste generated during the medical or surgical procedure in the bag.

\* \* \* \* \*